(12) United States Patent
Binner et al.

(10) Patent No.: US 8,186,997 B2
(45) Date of Patent: May 29, 2012

(54) METHOD FOR CLEANING THE ORAL CAVITY

(75) Inventors: Curt Binner, Furlong, PA (US); Megha Reddy, Lawrenceville, NJ (US)

(73) Assignee: McNeil-PPC, Inc., Skillman, NJ (US)

( * ) Notice: Subject to any disclaimer, the term of this patent is extended or adjusted under 35 U.S.C. 154(b) by 176 days.

(21) Appl. No.: 12/825,920

(22) Filed: Jun. 29, 2010

(65) Prior Publication Data

US 2011/0318713 A1    Dec. 29, 2011

(51) Int. Cl.
*A61C 17/00* (2006.01)
*A61C 3/00* (2006.01)

(52) U.S. Cl. .......................... 433/29; 433/216; 128/898

(58) Field of Classification Search .............. 607/88–93; 128/898; 433/25, 27, 29, 80, 119, 125, 142, 433/144, 116, 216
See application file for complete search history.

(56) References Cited

U.S. PATENT DOCUMENTS

| | | |
|---|---|---|
| 3,261,978 A | 7/1966 | Brenman |
| 3,309,274 A | 3/1967 | Brilliant |
| 3,711,700 A | 1/1973 | Westlund et al. |
| 3,732,416 A | 5/1973 | Audesse et al. |
| 5,382,163 A | 1/1995 | Putnam |
| 5,894,620 A | 4/1999 | Polaert et al. |
| 5,957,687 A | 9/1999 | Brilliant |
| 6,024,562 A | 2/2000 | Hibst et al. |
| 6,053,731 A | 4/2000 | Heckenberger |
| 6,485,300 B1 | 11/2002 | Muller et al. |
| 6,561,808 B2 | 5/2003 | Neuberger |
| 6,616,451 B1 | 9/2003 | Rizolu et al. |
| 6,862,771 B1 | 3/2005 | Muller |
| 6,902,397 B2 | 6/2005 | Farrell et al. |
| 7,223,270 B2 | 5/2007 | Altshuler et al. |
| 7,324,661 B2 | 1/2008 | Kemp et al. |
| 7,328,708 B2 | 2/2008 | Malak |
| 7,329,273 B2 | 2/2008 | Altshuler et al. |
| 2003/0156788 A1 | 8/2003 | Henning |
| 2004/0023184 A1 | 2/2004 | de Josselin de Jong et al. |
| 2004/0106081 A1 | 6/2004 | Karazivan et al. |

(Continued)

FOREIGN PATENT DOCUMENTS

WO      WO 92/06671    4/1992

(Continued)

OTHER PUBLICATIONS

Sagel et al, "Objective Quantification of Plaque Using Digital Image Analysis", Faller RV (ed): Assessment of Oral Health, Monogr Oral Sci. Basel, Karger, 2000, vol. 17, pp. 130-143.

*Primary Examiner* — Ahmed Farah

(57) ABSTRACT

A method of cleaning an oral cavity, the method including positioning a device suitable for detecting and removing plaque from a surface of the oral cavity within the oral cavity, cleaning and irradiating the surface of a tooth in the oral cavity, the tooth having applied thereto a fluorescent agent, with incident radiation of a wavelength effective to provide a fluorescent emission when contacted with the fluorescent agent on the tooth, collecting at least a portion of the fluorescent emission over a first time period, determining a first average fluorescent emission value (APV1), collecting at least a portion of the fluorescent emission over a second time period, determining a second average plaque value (APV2); and comparing the APV1 to the APV2.

15 Claims, 4 Drawing Sheets

U.S. PATENT DOCUMENTS

| | | |
|---|---|---|
| 2005/0053898 A1 | 3/2005 | Ghosh et al. |
| 2005/0170316 A1 | 8/2005 | Russell et al. |
| 2006/0085052 A1 | 4/2006 | Feuerstein et al. |
| 2006/0141421 A1 | 6/2006 | Braunecker et al. |
| 2006/0183071 A1 | 8/2006 | Hsueh |
| 2006/0257822 A1 | 11/2006 | Ghosh et al. |
| 2007/0038272 A1 | 2/2007 | Liu |
| 2007/0111166 A1 | 5/2007 | Dursi |
| 2007/0111167 A1 | 5/2007 | Russell et al. |
| 2007/0280888 A1 | 12/2007 | Fujikawa et al. |
| 2007/0298372 A1 | 12/2007 | Pinyayev et al. |
| 2008/0060148 A1 | 3/2008 | Pinyayev et al. |
| 2009/0226241 A1 | 9/2009 | McEwen et al. |
| 2011/0314618 A1* | 12/2011 | Binner et al. .................. 15/22.1 |
| 2011/0318712 A1* | 12/2011 | Reddy et al. .................. 433/216 |

FOREIGN PATENT DOCUMENTS

| | | |
|---|---|---|
| WO | WO 97/29714 | 8/1997 |
| WO | WO 2004/084752 A | 10/2004 |
| WO | WO 2006/047868 A | 5/2006 |
| WO | WO 2006/098719 A | 9/2006 |
| WO | WO 2007/111703 A | 10/2007 |
| WO | WO 2008/059435 A | 5/2008 |
| WO | WO 2008/088241 A | 7/2008 |
| WO | WO 2009/070344 A | 6/2009 |
| WO | WO 2009/134784 A | 11/2009 |
| WO | WO 2010/059484 A | 5/2010 |

* cited by examiner

METHOD FOR CLEANING THE ORAL CAVITY

FIELD OF THE INVENTION

This invention relates to methods for cleaning surfaces of an oral cavity including, e.g. teeth and gums.

BACKGROUND OF THE INVENTION

Biological deposits generally refer to deposits of material of biological origin, such as plaque, bacteria, tartar, and calculus that are generally regarded as undesirable for dental hygiene. Dental plaque is a complex organic deposit generated in part by the activity of bacteria upon surfaces of the oral cavity, such as on the teeth, or upon contamination from, for example, food deposits on the teeth, gums, tongue, or cheek. Plaque is an undesirable precursor to tooth decay and the development of dental caries.

It is desirable to detect plaque deposits in the oral cavity to direct action for removal, for example by using toothbrushes (manual or power), tooth floss, tooth picks, or oral irrigators, as detection indicates the areas at which dental cleaning effort should be focused. Such deposits can be difficult to detect in situ/in vivo on the teeth, gums, tongue, or cheek. It is especially important to detect dental plaque. For detection of plaque it is known to use fluorescence measurement, in which incident radiation is directed at the surfaces of the oral cavity, and fluorescence radiation having characteristics associated with the presence of biological deposits is emitted from the surfaces and is detected.

In the state of the art there are two general methods for detecting dental plaque. One method uses primary fluorescence, where the fluorescence of dental plaque or other dental material itself is monitored. The other method uses secondary fluorescence, where surfaces in the oral cavity suspected of bearing plaque are treated with a fluorescent label material which preferentially binds to dental plaque, and the fluorescence emission of the label material on the oral cavity surfaces to which it has bound is detected to indicate the presence of dental plaque. Also known are toothbrush heads having a bundle of optical fibers extending through it to direct incident radiation at a test tooth surface, and to collect emitted radiation from the test tooth surface.

A requirement of such methods is that incident radiation is directed at the surfaces of the oral cavity under examination and that consequent fluorescence emission radiation from those surfaces is collected. The amplitude of that radiation is a function of the amount of biological deposit located on the surface, as well as the distance the light source and detectors are from the surface. Consequently, the actual plaque value detected will fluctuate depending upon such factors, thereby resulting in a plaque value which may not truly depict the condition of plaque on the surface of the oral cavity. Known devices are not known to compensate for distances between the source of radiation and/or sensors and the surface of the oral cavity when determining the amount of biological deposit on the oral cavity surfaces.

Devices and methods for detecting and removing plaque in the oral cavity according to the invention described and claimed herein provide improved methods of cleaning teeth, particularly where plaque is detected and removed.

SUMMARY OF THE INVENTION

The invention is a method of cleaning an oral cavity, the method including positioning within the oral cavity a device suitable for detecting and removing plaque from a surface of the oral cavity, substantially simultaneously cleaning and irradiating the surface of at least one tooth in the oral cavity, the at least one tooth having applied thereto a fluorescent agent capable of binding to plaque on the surface of the at least one tooth, with incident radiation of a wavelength effective to provide a fluorescent emission when contacted with the fluorescent agent on the surface of the at least one tooth, collecting at least a portion of the fluorescent emission over a first time period, determining a first average fluorescent emission value (APV1) based on the fluorescent emission collected over the first time period, collecting at least a portion of the fluorescent emission over a second time period, determining a second average plaque value (APV2) based on the fluorescent emission collected over the second time period; and comparing the APV1 to the APV2.

DETAILED DESCRIPTION OF THE INVENTION

Figure 1:
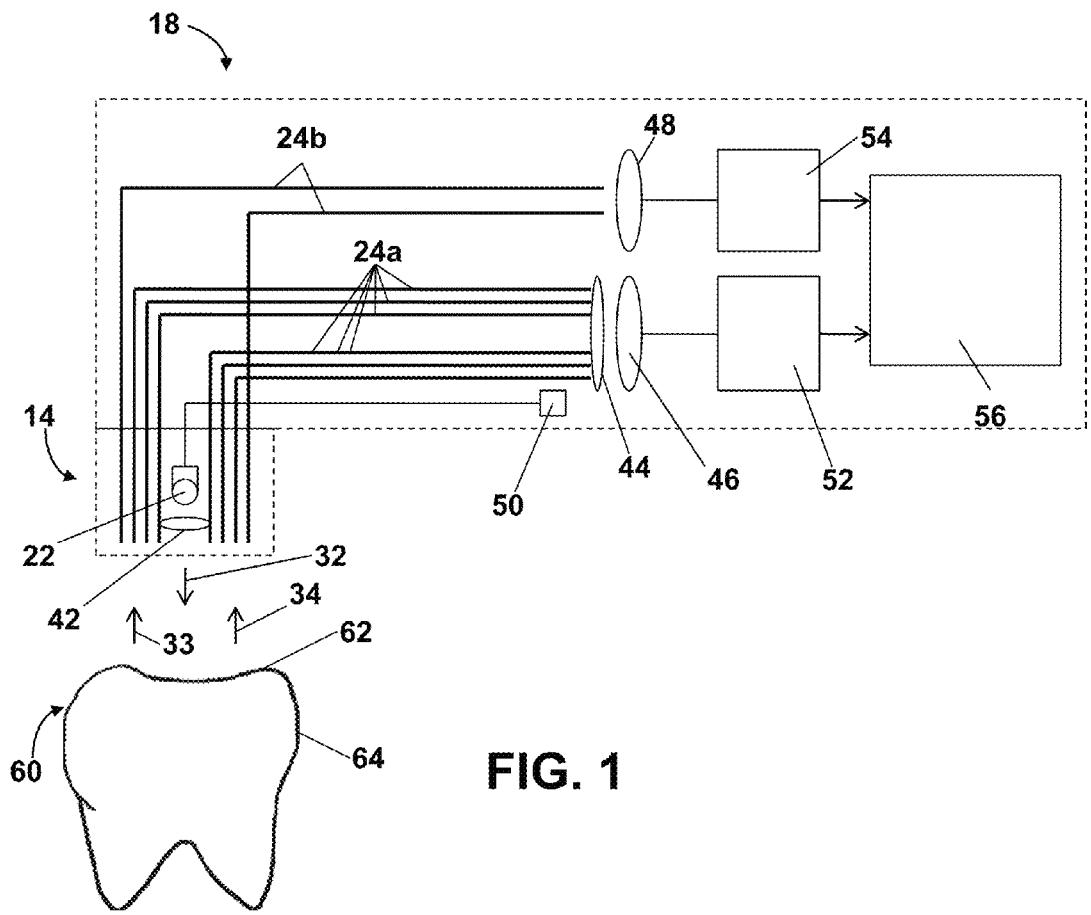
FIG. 1 is a schematic diagram of the operating principle of devices and methods of the present invention.

The following terms are used interchangeably both in the specification and the claims. APV is used interchangeably with "average plaque value". ACPV is used interchangeably with "average compensated plaque value". PMTP is used interchangeably with "predetermined maximum time period".

Methods for cleaning a surface of the oral cavity are provided, which may include detecting and removing plaque on the surface of the oral cavity, e.g. teeth and gums. The device comprises a radiation source for directing incident radiation onto a surface within the oral cavity to which a fluorescent agent has been bound. "Fluorescent agent", as used herein, means a composition or compound applied to the surface of the oral cavity, e.g. teeth or gums, which is capable of binding to plaque present on the surface in the oral cavity and is capable of providing a fluorescent emission when irradiated with incident radiation of a particular wavelength. By "binding" or "bound" to plaque, it is meant that the fluorescent agent is attached to plaque deposits on the surface of the oral cavity such that it will not be separated from the plaque deposit under conditions of cleaning as described herein. For example, brushing of the treated surface with a toothbrush, either manual or power, will not result in the fluorescent agent being removed from the surface unless the plaque to which it is attached is removed from the surface.

The radiation source typically may provide light having a peak wavelength of from about 450 to about 500 nanometers, although the range may vary depending upon the particular fluorescent agent applied to the surface of the oral cavity to be cleaned. The device may optionally include a filter for filtering incident radiation prior to contact with the surface of the oral cavity to be examined. The device also includes optical collectors for collecting fluorescent emission, and optionally reflected light, resulting from contact of the incident radiation with the treated surface. In certain embodiments, the optical collectors may comprise optical fibers or filaments. The device also includes an optical pathway for conveying the collected fluorescent emission and reflected light in the device. In certain embodiments, the optical pathway may comprise optical fibers. As such, optical fibers may serve both to collect and convey the reflected light and fluorescent emission.

The device further includes electrical components for sensing, or detecting, the optical light of the fluorescent emission, means for converting the optical light signal to an electrical signal and a data processor for manipulating the electrical signal correlating to the collected fluorescent emission taken over iterative intervals so as to determine an average plaque value. As such, plaque value, or average plaque value, as discussed and determined herein, is based upon and correlates to the fluorescent emission generated by contact of the incident radiation with the fluorescent agent and collected by the device over a particular time period.

In embodiments where both reflected light and fluorescent emission are collected, the device further includes electrical components for sensing the optical light signal of the reflective light and the fluorescent emission. In one embodiment, the optical light signals of the reflective light and the fluorescent emission are sensed, or detected, sequentially, but essentially simultaneously. By essentially simultaneously, it is meant that, while measurements are not taken exactly at the same time, the difference in time between detecting the reflective light and fluorescent light, respectively, is so small that the detection of each approximates the simultaneous reading. The device further comprises means for converting an optical light signal to an electrical signal, for example, a transducer. The devices may include means for amplifying or conditioning the electrical signal, thus providing a smoother or averaged signal, or a signal with reduced noise. The device also includes a data processor which may contain an analogue-to-digital converter for converting the electrical signal from an analogue format to a digital format. The processor then mathematically manipulates the electrical signal of the collected reflected light and fluorescent emission taken over iterative intervals so as to determine an average compensated plaque value (ACPV) over a particular time period. By "compensated plaque value", it is meant that the plaque value is determined taking into account the distance between the optical collector and the surface of the oral cavity being examined. As such, the compensated plaque value is determined as a function of the distance between the optical collector and the surface of the oral cavity at any given moment/reading. As a result of determining plaque value as a function of distance, the compensated plaque value so determined will be substantially the same for a particular surface at any particular moment/reading, irregardless of the actual distance between the radiation source and the surface of the oral cavity being cleaned. By substantially the same, it is meant that the determined compensated plaque value at any given distance will be statistically the same. The device may be used as a component of, or in combination with, oral cleaning devices such as toothbrushes, whether manual or power.

Methods of the present invention for cleaning surfaces in the oral cavity, e.g. teeth and gums, involve the use of a fluorescent agent applied to the surface in the oral cavity prior to cleaning. For example, fluorescein or salts thereof, e.g. sodium fluorescein, are known fluorescent agents and may be dispersed in a suitable medium, such as toothpaste, a dental gel, or a rinse containing the fluorescent agent. The fluorescent agent can be applied either by first rinsing the oral cavity with the fluorescent agent or by applying the toothpaste or dental gel containing the fluorescent agent. The plaque on the surfaces of the oral cavity retains an amount of fluorescent agent bound thereto that is proportionate to the amount of plaque on the surface. While fluorescein is one example of a fluorescent agent, other agents are known that will bind to plaque similar to fluorescein. The particular wavelength of the incident radiation used in methods and devices of the present invention will vary, depending on the particular fluorescent agent chosen.

After application of the fluorescent agent to the surface in the oral cavity to be cleaned, the user positions the device that is suitable for detecting and removing plaque from the surface of the oral cavity within the oral cavity and proceeds to clean the surface. The oral cavity may be partitioned into a plurality of sections, for example, from 4 to 12 sections, so that cleaning of the oral cavity can take place in stages, proceeding from one section to another until the entire surface in the oral cavity, e.g. teeth and/or gums, is cleaned. The number of sections into which the oral cavity is partitioned may be pre-selected and programmed into the device, as described herein below. Alternately, the number of sections may be determined on a continuous basis during cleaning, based on readings of average fluorescent emission being taken continuously throughout the cleaning process. In either case, the device itself provides a prompt to the user, for example, without limitation, auditory, visual, or vibratory, indicating that the user should move the device to another of the plurality of sections in the oral cavity.

In practice, the device is positioned within one of the plurality of sections of the oral cavity to be cleaned. The device substantially simultaneously cleans and irradiates a surface of at least one tooth in the section of the oral cavity being cleaned with incident radiation. The surface of the tooth in the section being cleaned and irradiated has applied thereto a fluorescent agent capable of binding to plaque on the surface of the at least one tooth. The surface is irradiated with incident radiation of a wavelength effective to provide a fluorescent emission when contacted with the fluorescent agent bound to the plaque on the surface of at least one tooth.

The method of the invention includes collecting at least a portion of the fluorescent emission from the surface being cleaned over a first time period and then determining a first average plaque value (APV1). The APV1 is the average plaque value based on multiple fluorescent emission readings collected over the first time period. At least a portion of the fluorescent emission is then collected over a second time period and is a second average plaque value (APV2) is determined based on multiple fluorescent emission readings collected over the second time period. The APV1 is then compared to the APV2. If the APV1 is greater than or equal to the APV2, the surface being cleaned in the section of the oral cavity is continuously, substantially simultaneously cleaned and irradiated for a predetermined maximum time period. As such time as the predetermined maximum time period has expired, the device is moved to another section within the oral cavity for cleaning. If the APV2 is less than the APV1, the device is moved and positioned within another of the plurality of sections and the steps of cleaning, irradiating, collecting the fluorescent emission, determining APV1 and APV2 and comparing the APV1 to the APV2 are repeated in the next section.

In certain embodiments, reflected light resulting from contact of the incident radiation with the treated surface is collected essentially simultaneously with the fluorescent emission. In these embodiments, the fluorescent emission values are compensated fluorescent emission values, as defined herein above.

Figure 2:
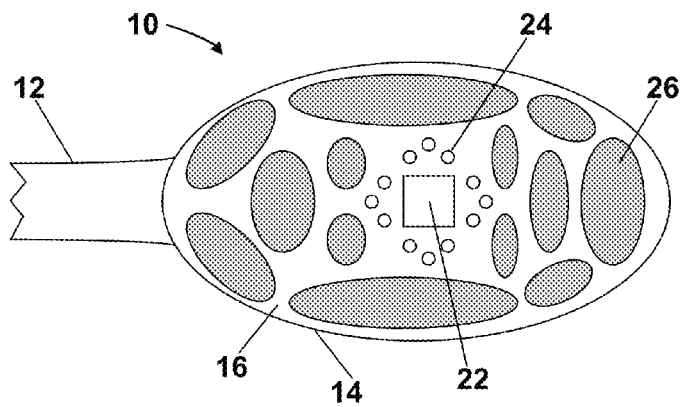
FIG. 2 shows a top plan view of an embodiment of the bristle face of a toothbrush head embodiment of the present invention.

FIG. 1 is a schematic diagram of the operating principle of methods and devices for cleaning surfaces of the oral cavity according to the present invention. The particular embodiment represented is a toothbrush, although other devices for use within the oral cavity also are contemplated by the invention. FIG. 2 is a plan view of a toothbrush head according to the invention, taken from the bristle side of the brush head. In the embodiment shown, toothbrush head portion 14, represented as a first dashed box on FIG. 1, includes, in addition to conventional bristle tufts 26 for cleaning teeth, radiation source 22 and optical fibers 24a and 24b for conveying reflected light 33 and fluorescent emission 34 resulting from contact of the surface of the oral cavity with the incident radiation. Head 14 also may include first optical filter 42, depending on the radiation source. Although stationary bristle tufts 26 for cleaning teeth are shown in FIG. 1, it is to be understood that the device for cleaning an oral cavity discussed herein could be a power toothbrush which could use methods of cleaning teeth and gums such as moving bristle tufts, ultrasonics, or radiation.

Electrical housing 18, represented as a second dashed box in FIG. 1, will contain other electrical components of a plaque detecting device located therein, as described herein above. In some embodiments, electrical housing 18 may reside in a handle portion of the cleaning device, for example a toothbrush handle. In the embodiment shown, optical fibers 24a and 24b extend from head 14 into electrical housing 18. Housing 18 also includes contained therein, second optical filter 44, first optical transducer 46, second optical transducer 48, first amplifier 52, second amplifier 54, data processor 56 and power source 50 for operating the electrical components.

FIG. 1 also shows a representative surface of the oral cavity, e.g. tooth 60, with top surface 62 and side surface 64. Though FIG. 1 shows device 10 directed at top surface 62 of tooth 60, it is to be understood that both top surface 62 and side surface 64 of tooth 60, may be contacted with incident radiation. In addition, such contact may be simultaneously at top surface 62 and side surface 64 of multiple teeth 60, depending on the brushing technique of the user. The cleaning device may also be directed at other surfaces in the oral cavity, such as those of the gums, tongue, or cheek.

In operation, prior to use of the cleaning device, the oral cavity is treated with a fluorescent label material, i.e. a fluorescent agent, which preferentially binds to dental plaque and which produces a fluorescent emission when exposed to incident radiation. Depending on the particular fluorescent agent chosen, the peak wavelength of the incident radiation may vary. In embodiments utilizing fluorescein or salts thereof, e.g. sodium fluorescein, the incident radiation may have a peak wavelength ranging from about 450 to about 500 nanometers. Once placed within the oral cavity, radiation source 22 emits light at a peak wavelength of from about 450 to about 500 nanometers (nm), or about 470 nanometers. The light may be passed through first optical filter 42, which removes substantially all light having wavelength above about 510 nm. As shown, incident radiation 32 from radiation source 22 is directed at top surface 62 of tooth 60, although as discussed above, the incident radiation may contact multiple surfaces of the oral cavity, e.g. the teeth. Upon contact with the surface, incident radiation interacts with the fluorescent agent that has bonded to plaque located on the surfaces of tooth 60. The fluorescent agent then produces a fluorescent emission 34 having a peak wavelength of from about 520 to about 530 nanometers. A first portion of fluorescent emission 34 provided by the fluorescent agent is collected by optical fibers 24a and conveyed in the device by optical fibers 24a for further mathematical processing. Incidentally, a second portion of reflected light 33 is essentially simultaneously collected and conveyed with the first portion of fluorescent emission 34. Fluorescent emission 34 is passed through a second optical filter 44, which removes substantially all light of wavelengths below about 515 nm, ensuring that essentially no reflected light is passed to the data processor 56. The now filtered fluorescent emission 34 passes through first optical transducer 46 in the form of a photodiode, which converts the optical light signal into an electrical signal. The electrical signal is passed through first amplifier 52 to increase the electrical signal being passed to data processor 56.

A first portion of the reflected light is collected by optical fibers 24b and conveyed in the device by optical fibers 24b for further mathematical processing. Incidentally, a second portion of fluorescent emission 34 is collected and conveyed with the first portion of reflected light. The second portion of fluorescent emission 34 and the first portion of the reflected light are conveyed through second optical transducer 48, in the form of a photodiode, which converts the optical light signal into an electrical signal. While it is an option to provide an optical filter to remove substantially all of the fluorescent emission prior to passing through second optical transducer 48, in the embodiment shown, neither the second portion of the fluorescent emission, nor the first portion of reflected light is filtered prior to their passing through second optical transducer 48, as these signals are used to measure the distance from the radiation source 22 to the surface of tooth 60. The unfiltered electrical signal is passed through second amplifier 54 to increase the electrical signal being passed to data processor 56.

Electronic parts that may be used in plaque detecting device 10 may include Taos TSL12S-LF photodiodes, Opamp Analog AD8544ARZ amplifiers, Semrock fluorescence filters (FF01-500-LP, FF01-475/64), and Atmel ATMEGA8L-8AU microprocessor.

Data processor 56 performs a mathematical manipulation on the inputs from first optical transducer 46 and second optical transducer 48. In the mathematical manipulation, the electrical signal resulting from filtered fluorescent emission 34 is modified to account for the electrical signal received from the unfiltered electrical signal that was used to determine distance from the tip of optical fiber 24b, i.e. the optical collector, to the surface of tooth 60. The relationship between the two signals is experimentally determined by measuring their respective signal strengths at known distances from the surface of objects coated with a fluorescent agent. The result of the mathematical manipulation is a corrected electrical signal which results in a compensated plaque value, as that term is described and defined herein.

FIG. 2 shows a plan view of a first embodiment of a device of the present invention. As shown, device 10 is in the form of a toothbrush with a handle portion 12 and a head portion 14. FIG. 2 shows the bristle face 16 of device 10. Bristle face 16 of head portion 14 is shown as generally oval in shape, but it is important that bristle face 16 may be in shapes such as triangle, square, rectangle, trapezoid, and other polygons, or circle, ellipse, crescent, deltoid, asteroid, or other curved shapes.

Radiation source 22, optical collectors and conveyors 24 and cleaning tufts 26 are located on bristle face 16. Radiation source 22, preferably in the form of a light emitter such as a light-emitting diode (LED), directs incident excitation radiation at the surfaces of the teeth to be cleaned. Optical collectors and conveyors 24, typically in the form of optical fibers, collect the fluorescent radiation emitted from the teeth. The optical fibers may be made of glasses such as silica, but may be made of other materials, such as fluorozirconate, fluoroaluminate, and chalcogenide glasses, but may also be in the form of plastic optical fibers (POFs).

Cleaning tufts 26 are made of approximately 20 to 50 individual bristles arranged on bristle face 16 in a manner to optimize cleaning of the surfaces of the teeth. FIG. 1 shows one arrangement of tufts 26 on bristle face 16. It is to be understood that the arrangement of tufts 26 on bristle face 16 is not limiting in the scope of the present invention. Typical tufts are approximately 0.063 inches (1.6 mm) in diameter, with a cross-sectional area of approximately 0.079 inches$^2$ (2 mm$^2$). The diameters of commonly used bristles are: 0.006 inch (0.15 mm) for soft bristles, 0.008 inch (0.2 mm) for medium bristles, and 0.010 inch (0.25 mm) for hard bristles.

A general problem in the recognition of caries, plaque or bacterial infection on teeth with the above-described method is found in that the detected fluorescent radiation can be disruptively superimposed with daylight or the artificial room lighting. This environmental light can likewise be reflected from the tooth 60 and thus collected by optical fibers 24$a$ and 24$b$. The spectral region of the environmental light lying in the detection region in accordance with the invention results in a background signal, i.e. noise, which restricts the sensitivity of plaque detection.

This problem is effectively resolved in accordance with the invention in that the incident radiation 32 generated by radiation source 22 is periodically modulated. In this case, because of the short duration of the excited state the fluorescent emission 34 follows the intensity of the excitation radiation practically instantaneously. In contrast, the environmental light is not periodically modulated and is superimposed on the detected emission 34 solely as a constant component. For evaluation of the emission 34, now only the radiation modulated with the corresponding frequency is employed as detection signal and evaluated. In this way, the constant component of the environmental light is quasi-filtered out and plaque is detected virtually independently of the environmental light. Since the environmental light is, however, modulated slightly with the frequency of the mains voltage, there should be chosen as modulation frequency for the incident radiation 32 at a frequency which differs distinctively from the mains voltage frequency and preferably lies in the range between 100 Hz and 200 kHz.

The devices and methods for detecting and removing plaque in the oral cavity may also be used as part of, or in combination with, oral care systems which track the health of the oral cavity. Such systems can record plaque levels on teeth, gum, tongue, or cheek surfaces, before and after cleaning operations, as well as the track the plaque of levels over time, reporting the results to the user, or to dental care professionals.

Figure 3:
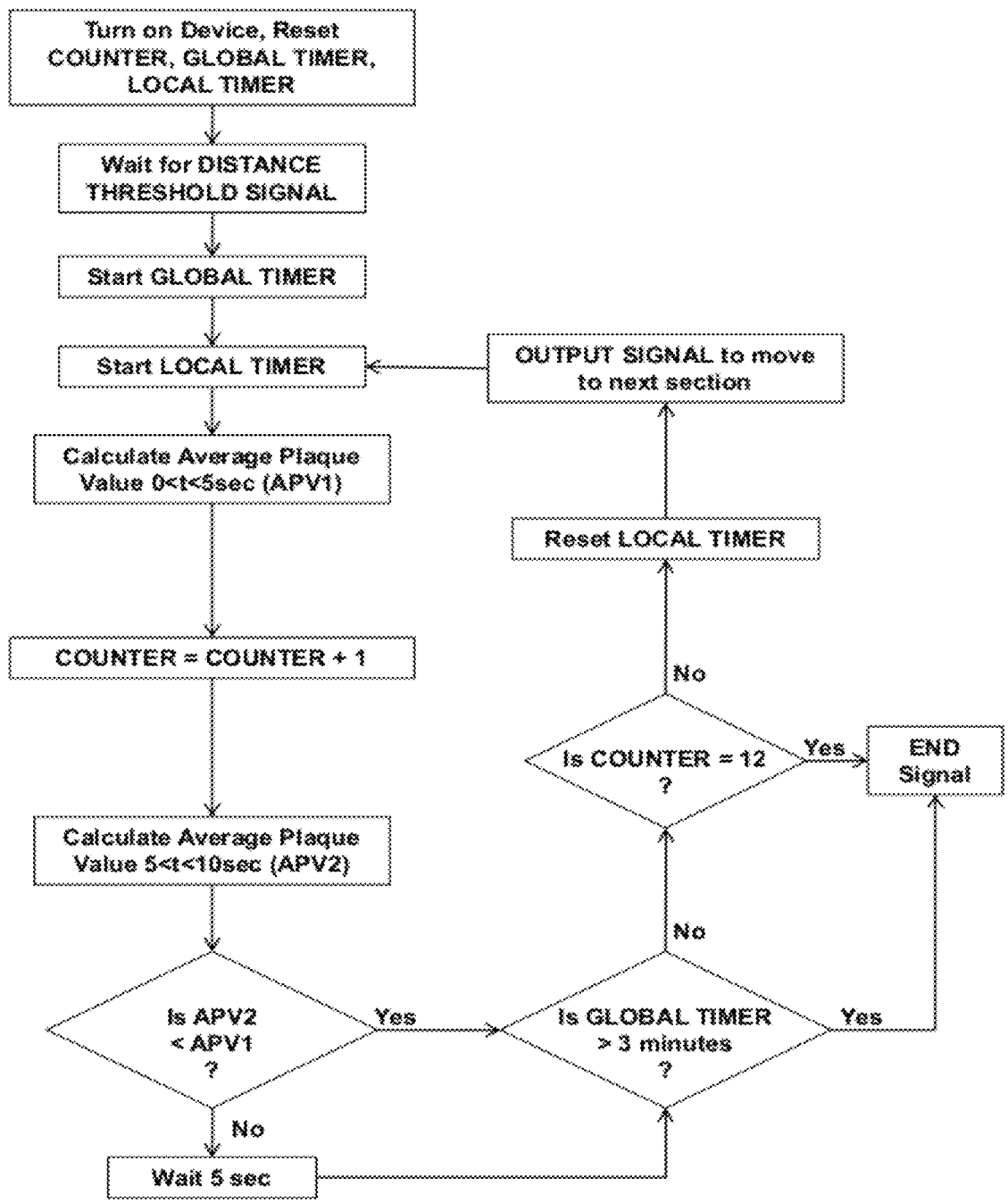
FIG. 3 illustrates an embodiment of a method of the present invention.

FIG. 3 illustrates a first embodiment method of the present invention. In this embodiment, used to clean teeth, the user is instructed to divide the teeth cleaning operation into a number of sections, and to move from section to section upon receiving an OUTPUT SIGNAL from oral cleaning device 10. For illustrative purposes, and not meant to be limiting in scope, reference is made to FIG. 1 and the embodiment shown in FIG. 3 uses twelve (12) sections of cleaning: three (3) for the front side of the top teeth, three (3) for the backside of the top teeth, three (3) for the front side of the bottom teeth, and three (3) for the backside of the bottom teeth. The order in with the sections are cleaned is not critical to the performance of oral cleaning device 10.

In the first step, oral cleaning device 10 is turned on, and an internal COUNTER, used to track the number of sections cleaned, a GLOBAL TIMER, and a LOCAL TIMER, are set to zero. Progressing to the next step, incident radiation from radiation source 22 is directed at top surface 62 or side surface 64 of a tooth 60 (or teeth) in the section being cleaned. Processor 56 waits until the strength from the unfiltered electrical signal that was used to determine distance from the radiation source 22 to the surface of tooth 60 is above a preset DISTANCE THRESHOLD SIGNAL. This is to insure that radiation source 22 is positioned within close proximity to the top surface 62 or side surface 64 of tooth 60. When the strength from the unfiltered electrical signal is above the preset DISTANCE THRESHOLD SIGNAL, the program progresses to the next steps, and both the GLOBAL TIMER and the LOCAL TIMER are started. If, at any point in the cleaning process, DISTANCE THRESHOLD SIGNAL falls below the preset DISTANCE THRESHOLD SIGNAL, both the GLOBAL TIMER and the LOCAL TIMER are stopped, and restarted when the strength from the unfiltered electrical signal rises above the preset DISTANCE THRESHOLD SIGNAL. The GLOBAL TIMER is predetermined and set to a maximum global cleaning time period (MGCTP) in which the entire oral cavity will be cleaned.

Progressing to the next step, processor 56 initiates the algorithm on the inputs from first optical transducer 46 and second optical transducer 48, resulting in a corrected electrical signal. An APV is calculated from time 0 on the LOCAL TIMER to a predetermined first time period and recorded as APV1. The predetermined first time period could be 5 seconds (as shown in FIG. 3), or could be other values such as, but not limited to, 10, 5, 4, 2, 1, 0.5, 0.25, or 0.01 seconds. In some embodiments, the APV may be calculated by taking data at intervals such as 1, 0.5, 0.25, 0.125, 0.1, 0.05 0.025, 0.0125, 0.01, or 0.005 seconds from time 0 to the predetermined first time period, and averaging the corrected electrical signal values over the number of data points measured. The time intervals for data recording may be regular, or can be randomly chosen over the predetermined first time period.

In the next step of the program, the value of COUNTER is increased by 1. Next, a second average plaque value is calculated from the end of the first predetermined time period to a predetermined second time period on the LOCAL TIMER and recorded as APV2. The predetermined second time period could be 5 seconds (as shown in FIG. 3), or could be other values such as, but not limited to, 15, 12, 10, 8, 6, 5, 3, 2, 1, or 0.001 seconds. The APV2 may, in some embodiments, be calculated by taking data at intervals such as 1, 0.5, 0.25, 0.125, 0.1, 0.05 0.025, 0.0125, 0.01, or 0.005 seconds from the end of the predetermined first time to the predetermined second time period, and averaging the corrected electrical signal values over the number of data points measured. The time intervals for data recording may be regular, or can be randomly chosen over the predetermined second time period.

Next, in a first decision block, the APV2 is compared to the APV1. If the APV2 is less than the APV1, the processor moves to a second decision block, as described below.

If the APV1 is greater than or equal to the APV2, the program waits for a predetermined third time on the LOCAL TIMER. The third time period is a local maximum time period for cleaning a particular section of the oral cavity. During the predetermined third time period, the user continues to clean the teeth in the section being cleaned to insure adequate cleaning time and plaque removal for the section being cleaned. Predetermined third time could be 10, 7.5, 5 (as in FIG. 3), 4, 3, 2, 1, or 0.5 seconds, and may be determined by routine experimentation with the oral cleaning device. In the embodiment shown in FIG. 3, the insured adequate brushing time for each section is 5 seconds, and the maximum cleaning time in each section is 15 seconds.

Upon expiration of the predetermined third time period, or if APV2 is less than APV1, the operating program in processor 56 progresses to the second decision block. The value of the running time in the GLOBAL TIMER is compared to the MGCTP. If the value of the running time in the GLOBAL TIMER is greater than the MGCTP, the operating program in processor 56 has an END signal sent to the user to inform the user that the cleaning process is complete. It is important to note that the MGCTP must be greater than the product of the number of preset sections and the maximum time in each section. In the case of the embodiment shown in FIG. 3, the number of preset sections is twelve (12), and the maximum time in each section is fifteen (15) seconds. So, the MGCTP in the embodiment shown in FIG. 3 is 180 seconds (3 minutes).

If the value of the running time in the GLOBAL TIMER is less than the MGCTP, the operating programming processor 56 progresses to the third decision block. In this decision block, the value of COUNTER is compared to the preset number of sections that are being cleaned. If the COUNTER is equal to the preset number of sections, the operating program in processor 56 has an END signal sent to the user to inform the user that the cleaning process is complete. As mentioned earlier, the embodiment shown in FIG. 3 uses twelve (12) sections of cleaning.

If the COUNTER is less than the preset number of sections, the operating program in processor 56 progresses to the next step. Here, the LOCAL TIMER is reset to zero, and the operating program in processor 56 has an OUTPUT SIGNAL sent to the user to inform the user to move the oral cleaning device 10 to the next section for cleaning. As shown is FIG. 3, the operating program in processor 56 progresses to the next step, where the LOCAL TIMER is started, and the program begins a second loop.

The process continues until the cleaning operation is completed in all sections. The END signal sent to the user to inform the user that the cleaning process is complete, as well as the OUTPUT SIGNAL sent to the user to inform the user to move the oral cleaning device 10 to the next section for cleaning, may be in a number of forms. These signals may be in forms directed to any of the five senses: sight, sound, touch, smell, or taste. For example, the handle portion 12 of oral cleaning device 10 may have a light, or a series of lights, on its surface, or embedded in the surface. The lights may be off while the user is cleaning each section with device 10. The OUTPUT SIGNAL may be used illuminate the light(s), informing the user it is time to move to the next section. The END signal sent to the user to inform the user that the cleaning process is complete, may be used to have the light(s) flash.

In another embodiment, lights of two colors can be used. Here, an illuminated light of a first color informs the user to remain in the section they are currently cleaning. When it is time to move to a new section, the OUTPUT SIGNAL may be used to dim the light of a first color, and illuminate a light of a second color. The END signal may be used to illuminate all of the light(s), or have all of the light(s) flash.

Oral cleaning device 10 may use a sound, or a series of sounds, in a similar manner. Changing volume, pitch, tone, or frequency are all possible outcomes from OUTPUT SIGNAL and END signal. In other embodiments, vibratory motions can be used to inform the user to move from section to section, or to inform them that cleaning is complete.

Figure 5:
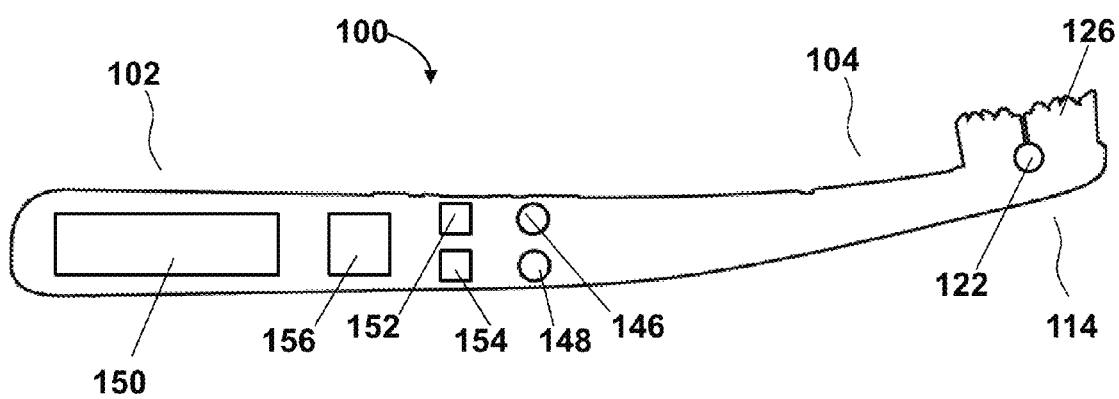
FIG. 5 is a cross-sectional view of an embodiment of a device for use in cleaning surfaces of the oral cavity according to the present invention.

FIG. 5 is a cross-sectional view of an embodiment of a device 100 for use in cleaning surfaces of the oral cavity according to the present invention. The particular embodiment represented is a toothbrush, although other devices for use within the oral cavity also are contemplated by the invention. As shown in FIG. 6, device 100 has a handle portion 102, a neck portion 104, and a toothbrush head portion 114. Toothbrush head portion 114 includes bristle tufts 126 for cleaning teeth and radiation source 122. Handle portion 102 is hollow, and optical transducers 146 and 148, amplifiers 152 and 154, data processor 156 and power source 150 are contained therein.

The present invention may be better understood with reference to the following examples.

EXAMPLES

Example 1

Determination of the Compensated Plaque Value

A plaque detecting toothbrush was created by modifying the head of a manual toothbrush by inserting a blue light-emitting diode (LED) facing outwards from the head, allowing the light from the LED to illuminate the tooth surface. The LED was surrounded by an array of 12 fiber optic filaments, also pointed towards the tooth surface in the area illuminated by the blue LED. The fiber optics passed through the neck of the toothbrush to a pair of photo sensors (Taos TSL12S-LF) contained in the handle section of the toothbrush. The fibers were separated into two groups. One group passed through an optical filter (Semrock FF01-500/LP) that allowed only wavelengths above 515 nm to pass, while the second group allowed all wavelengths to pass, i.e. no optical filter was utilized. The filtered light represented the plaque value while the unfiltered light was used to interpret the distance between the optical collector, i.e. the tips of the optical fibers, and the surface of the tooth. The output of the photo sensors were connected to amplifiers (Analog devices AD8544ARZ) which in turn were connected to an 8 bit microcontroller (Atmel ATMEGA8L-8AU). The microcontroller contained two 10 bit analog to digital converters that allowed the information to be manipulated in a digital format within the microcontroller.

Using this apparatus, experiments were performed by using Typodent teeth models coated with a simulated plaque material containing a fluorescent material. The artificial plaque was painted onto the tooth surfaces in a way that approximated the manner in which plaque grows in the human mouth. The experiments consisted of positioning the optical collectors, e.g. the tips of fiber optic filaments, at varied distances from the tooth surface so as to enable a relationship to be created between the distance and the plaque value.

The prototype device was operated with the following set of parameters:

Sampling at 500 Hz (0.002 seconds), sequentially taking 4 measurements in repeating succession.

Averaging every 20 data points per output data value.

Device powered by 8-bit microcontroller at 7 MHz clock speed.

RS232 readout of data to a spreadsheet, and

Ambient light compensation.

The device was placed at distances between 0 and 10 mm from the surface of the model tooth surface. Readings were taken with Distance LED on, Distance LED off, Plaque LED on, and Plaque LED off. The value of the signals for Total Plaque and Total Distance were calculated at each distance using:

Total Plaque=Plaque LED on−Plaque LED off (I)

Total Distance=Distance LED on−Distance LED off (II)

Table I shows the measured/calculated values for Plaque LED on, Plaque LED off, Total Plaque, Distance LED on, Distance LED off, Total Distance.

TABLE I

Distance and Plaque readings from prototype oral cleaning device.

| Distance (mm) | Plaque LED On | Plaque LED Off | Total Plaque A | Distance LED On | Distance LED Off | Total Distance B |
|---|---|---|---|---|---|---|
| 0 | 331.48 | 125.26 | 206.22 | 242.74 | 80.30 | 162.44 |
| 0.5 | 356.15 | 129.00 | 227.15 | 268.80 | 83.15 | 185.65 |
| 1.0 | 355.63 | 129.53 | 226.10 | 285.68 | 81.84 | 203.84 |
| 1.5 | 345.75 | 126.58 | 219.17 | 291.42 | 80.96 | 210.46 |
| 2.0 | 337.68 | 128.27 | 209.41 | 295.05 | 82.95 | 212.10 |
| 2.5 | 327.62 | 127.24 | 200.38 | 295.38 | 81.05 | 214.33 |
| 3.0 | 316.36 | 127.87 | 188.49 | 287.32 | 81.91 | 205.41 |
| 3.5 | 300.70 | 122.00 | 178.70 | 278.04 | 77.11 | 200.93 |
| 4.0 | 296.38 | 127.90 | 168.48 | 275.14 | 81.41 | 193.73 |
| 4.5 | 277.42 | 120.84 | 156.58 | 260.42 | 76.53 | 183.89 |
| 5.0 | 273.38 | 128.21 | 145.17 | 257.83 | 81.04 | 176.79 |
| 5.5 | 220.13 | 83.10 | 137.03 | 223.33 | 54.00 | 169.33 |
| 6.0 | 258.05 | 128.67 | 129.38 | 242.81 | 82.48 | 160.33 |
| 6.5 | 249.26 | 127.68 | 121.58 | 233.68 | 81.00 | 152.68 |
| 7.0 | 241.89 | 128.50 | 113.39 | 225.61 | 82.33 | 143.28 |
| 7.5 | 236.22 | 129.06 | 107.16 | 219.78 | 81.61 | 138.17 |
| 8.0 | 230.22 | 129.44 | 100.78 | 212.61 | 81.56 | 131.05 |
| 8.5 | 225.94 | 129.59 | 96.35 | 208.47 | 82.24 | 126.23 |
| 9.0 | 216.50 | 128.35 | 88.15 | 200.35 | 81.40 | 118.95 |
| 9.5 | 214.35 | 129.00 | 85.35 | 195.95 | 81.80 | 114.15 |
| 10.0 | 212.87 | 131.33 | 81.54 | 194.47 | 82.93 | 111.53 |

The value of Column A (Total Plaque) was plotted against Column B (Total Distance). The resulting line was curve fitted to the follow straight line equation:

Total Plaque=1.304(Total Distance)−66.61 (III)

Since the value of Total Plaque at a distance of 1 mm from the surface of the model tooth surface was 226, a Compensated Plaque Value (CPV) was determined using:

CPV=226+(1.304(Total Distance)−66.61)/Total Plaque (IV)

TABLE II

CPV as a function of distance for oral cleaning device.

| Distance (mm) | Total Plaque A |
|---|---|
| 0 | 226.70 |
| 0.5 | 226.77 |
| 1.0 | 226.88 |
| 1.5 | 226.95 |
| 2.0 | 227.00 |
| 2.5 | 227.06 |
| 3.0 | 227.15 |
| 3.5 | 227.09 |
| 4.0 | 227.10 |
| 4.5 | 227.11 |
| 5.0 | 227.13 |
| 5.5 | 227.12 |
| 6.0 | 227.10 |
| 6.5 | 227.09 |
| 7.0 | 227.06 |
| 7.5 | 227.06 |
| 8.0 | 227.04 |
| 8.5 | 227.02 |
| 9.0 | 227.01 |
| 9.5 | 226.97 |
| 10.0 | 226.97 |
| AVERAGE | 227.02 |
| Std. Dev. | 0.12 |

The table shows the average calculated CPV independent of distance is 227.02, with a standard deviation of 0.012 (0.05%). So, the value of the plaque reading has been compensated for, taking into account the distance from the optical collector to the surface of the model tooth.

Example 2

Use of the Oral Cleaning Device

The device described in Example 1 was used in a study to clean human teeth. Participants in the study did not perform any oral hygiene for 18-24 hours before the study was performed. The study was conducted using surrogate brushing by a hygienist using the American Dental Association-approved Bass Method. The mouth was divided into 12 equal sections so that each section could be analyzed individually. The maximum total time period for brushing of each section was predetermined and set to 10 seconds to simulate an entire mouth brushing time of two minutes. During brushing, the data produced with the device was output via serial communication to a PC that recorded the data.

Figure 4:
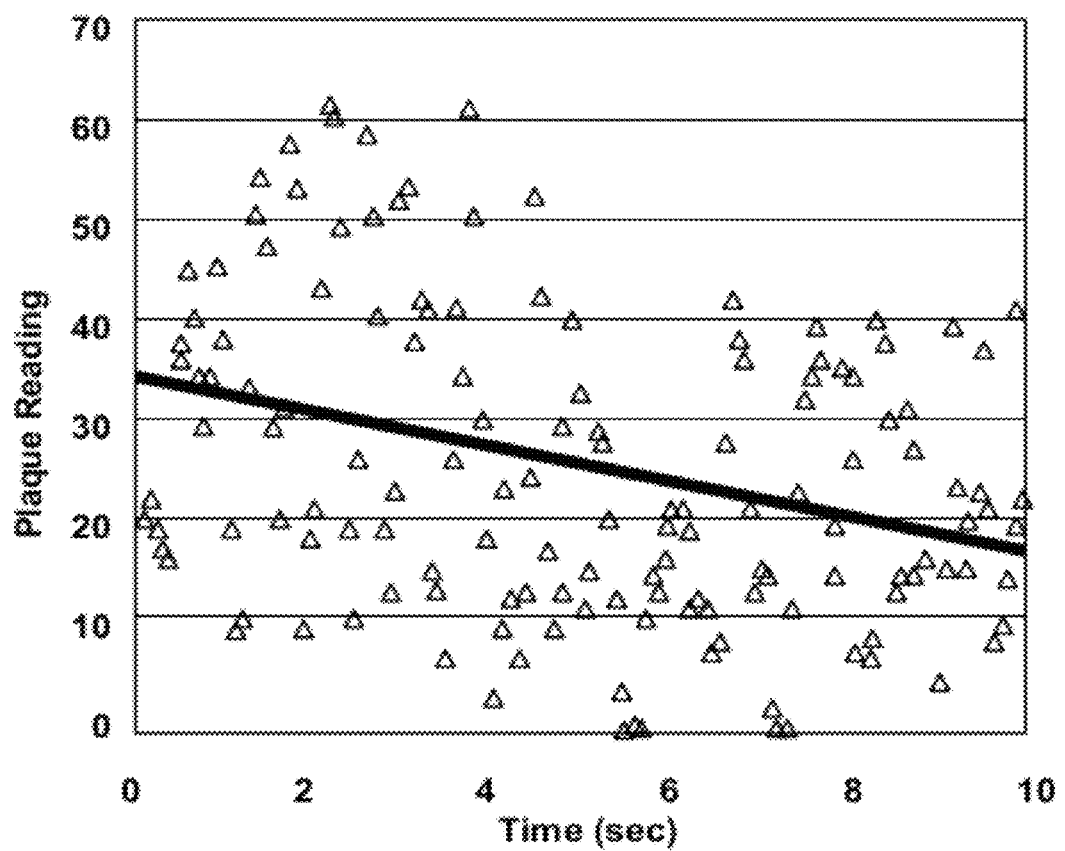
FIG. 4 is a sample plot of data produced from an oral cleaning device of the present invention.

FIG. 4 is a sample plot of the data produced from the device during the 10 second brushing of a particular section of the mouth. The data oscillates up and down because the detecting portion of the brush is repeatedly traveling over areas within the section containing different levels of plaque. A linear trend line drawn through the data shows the reduction of plaque during the 10 second time period.

While the foregoing description and drawings represent exemplary embodiments of the present invention, it will be understood that various additions, modifications and substitutions may be made therein without departing from the spirit and scope of the present invention. One skilled in the art will appreciate that the invention may be used with many modifications of structure, arrangement, proportions, materials, and components and otherwise, used in the practice of the invention, which are particularly adapted to specific environments and operative requirements without departing from the principles of the present invention. For example, elements shown as integrally formed may be constructed of multiple parts, or elements shown as multiple parts may be integrally formed, the operation of elements may be reversed or otherwise varied, or the size or dimensions of the elements may be varied. Therefore, the presently disclosed embodiments are to be considered in all respects as illustrative and not restrictive, the scope of the invention being indicated by the appended claims, and not limited to the foregoing description.

What is claimed is:

1. A method for cleaning an oral cavity, said method comprising:
 a. positioning within a section of said oral cavity a device suitable for detecting and removing plaque from a surface of at least one tooth in said oral cavity, b. substantially simultaneously cleaning and irradiating said surface of at least one tooth in said oral cavity, said at least one tooth having applied thereto a fluorescent agent capable of binding to plaque on said surface of said at least one tooth, with incident radiation of a wavelength effective to provide a fluorescent emission when contacted with said fluorescent agent on said surface of said at least one tooth, c. collecting at least a portion of said fluorescent emission over a first time period, d. determining a first average plaque value (APV1) based on said fluorescent emission collected over said first time period, e. collecting at least a portion of said fluorescent emission over a second time period, f. determining a second average plaque value (APV2) based on said fluorescent emission collected over said second time period; and g. comparing said APV1 to said APV2, wherein reflected light resulting from contact of said incident radiation with said surface is collected essentially simultaneously with said fluorescent emission and said APV1 and APV2 to determine average compensated plague value (ACPV) for said APV1 and APV2.

2. The method of claim 1 wherein, if said APV2 is less than said APV1, said device is positioned within another section of said oral cavity.

3. The method of claim 1 wherein, if said APV1 is greater than or equal to said APV2, said surface in said section is continuously substantially simultaneously cleaned and irradiated for a predetermined maximum time period.

4. The method of claim 3 wherein said predetermined maximum time period is from about 0.5 to about 15 seconds.

5. The method of claim 1 wherein said fluorescent agent comprises fluorescein or a salt thereof.

6. The method of claim 5 wherein said incident radiation has a peak wavelength of from about 450 to about 500 nanometers.

7. The method of claim 5 wherein said portion of said fluorescent emission has a peak wavelength of from about 520 to about 530 nanometers.

8. The method of claim 1 wherein said first time period is from about 0.01 to about 10 seconds.

9. The method of claim 1 wherein said second time period is from about 0.001 to about 15 seconds.

10. The method of claim 1 wherein said reflected light is simultaneously conveyed with said fluorescent emission through an optical filter prior to conversion of an optical signal of said fluorescent emission to an electrical signal of said fluorescent emission, said filter removing light having a wavelength of above about 515 nanometers.

11. The method of claim 1 wherein said compensated APV1 and APV2 are determined as a function of the distance between the point of collection of said fluorescent emission and said surface of said oral cavity.

12. The method of claim 11 wherein said cleaning is effected by sonification, pressurized water and brushing.

13. The method of claim 12 wherein said brushing is effected by a power toothbrush or a manual toothbrush.

14. The method of claim 1 wherein said cleaning is effected by sonification, pressurized water and brushing.

15. The method of claim 14 wherein said brushing is effected by a power toothbrush or a manual toothbrush.

* * * * *